US010988443B2

(12) United States Patent
Treiber

(10) Patent No.: US 10,988,443 B2
(45) Date of Patent: *Apr. 27, 2021

(54) METHODS FOR IMPROVED PRODUCTION OF VITAMINS $D_2$ AND $D_3$

(71) Applicant: NUCELIS LLC, San Diego, CA (US)

(72) Inventor: Laszlo R. Treiber, San Diego, CA (US)

(73) Assignee: NUCELIS LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/459,029

(22) Filed: Jul. 1, 2019

(65) Prior Publication Data

US 2019/0322621 A1    Oct. 24, 2019

Related U.S. Application Data

(63) Continuation of application No. 15/537,391, filed as application No. PCT/US2015/066829 on Dec. 18, 2015, now Pat. No. 10,336,694.

(60) Provisional application No. 62/093,904, filed on Dec. 18, 2014.

(51) Int. Cl.
 *C07C 401/00* (2006.01)
 *A23L 33/155* (2016.01)
 *C07J 9/00* (2006.01)

(52) U.S. Cl.
 CPC .......... *C07C 401/00* (2013.01); *A23L 33/155* (2016.08); *C07J 9/00* (2013.01); *A23V 2250/7104* (2013.01); *A23V 2250/7106* (2013.01); *C07C 2601/14* (2017.05); *C07C 2602/24* (2017.05)

(58) Field of Classification Search
 CPC ......... C07J 15/005; C07J 9/00; C07C 401/00; C07C 2601/14; C07C 2602/24; A23L 33/155; A23V 2250/7106; A23V 2250/7104
 See application file for complete search history.

(56) References Cited

U.S. PATENT DOCUMENTS

| 3,176,029 | A | 3/1965 | Bharucha et al. |
| 3,367,950 | A | 2/1968 | Salwa et al. |
| 3,575,831 | A | 4/1971 | Pfoertner |
| 4,388,242 | A | 6/1983 | Malatesta et al. |
| 4,772,433 | A * | 9/1988 | Hesse ...................... C07C 29/40 544/233 |
| 10,336,694 | B2 * | 7/2019 | Treiber ...................... C07J 9/00 |
| 2013/0149385 | A1 | 6/2013 | Mousa |

FOREIGN PATENT DOCUMENTS

| CN | 107207429 A | 9/2017 |
| DE | 297812 A5 | 1/1992 |
| EP | 0118903 A1 | 9/1984 |
| EP | 3233793 A1 | 10/2017 |
| WO | 2008128783 A2 | 10/2008 |
| WO | 2016100892 A1 | 6/2016 |

OTHER PUBLICATIONS

The Office Action issued by the JPO in Japanese Patent Application No. 2017-533507 dated Sep. 10, 2019—incl Eng Lang transl (11 pages total).
Okabe Vitamin D2 From Ergosterol [ 9,10-Secoergosta-5,7,10(19),22-tetraen-3-ol,(3β)- from Ergosta-5,7,22-trien-3 ol,(3β)- ]. Org Synth, 1999;76:275-286.
"Organic Acids and Bases and Some of Their Derivatives", chapter 15 from the book entitled "Introduction to Chemistry: General, Organic, and Biological", 2012 (102 pages).
The First Exam Report issued by the Patent Office of India in Patent Application No. 201727025126 dated Feb. 7, 2020—incl Engl lang transl (6 pages total).
Communication pursuant to Rule 114(2)EPC issued in European Patent Application 15871215.8 forwarding 3rd party observations dated Feb. 25, 2019 (58 pages total).
The Extended European Search Report issued in EP 15871215 dated Jun. 19, 2018.
The International Preliminary Report on Patentability issued in PCT/US2015/066829 dated Jun. 20, 2017 (6 pages).
The International Search Report and Written Opinion issued in PCT/US2015/066829 dated Mar. 4, 2016 (7 pages).
Office Action issued in Japanese Patent Application 2017-533507 dated Jun. 16, 2020—incl Engl lang transl (8 pages total).
Hirsch, Vitamin D. in Kirk-Othmer Encyclopedia of Chemical Technology, Copyright John Wiley & Sons, Inc., Dec. 4, 2000; 1-34.
Kaushik et al., Development of an analytical protocol for the estimation of vitamin D2 in fortified toned milk. Food Chem. May 15, 2014;151:225-230.
Olds et al., Action Spectrum for Vitamin D Synthesis. NIWA UV Workshop, Poster 53, Queenstown Apr. 7-9, 2010:2 pages.
Tian and Holick, Catalyzed Thermal Isomerization between Previtamin D3 and Vitamin D3 via β-Cyclodextrin Complexation*. J Biol Chem. Apr. 14, 1995;270(15):8706-8711.
Yates et al.,"Precholecalciferol Formation by an Invertebrate, Psammechinus Miliaris". in Vitamin D: Molecular, cellular and Clinical Endocrinology. Proceedings of the Seventh Workshop on Vitamin D, © 1988 Walter de Gruyter & Co., Berlin • New York, Apr. 1988, pp. 83-92.
Zhu and Okamura, Synthesis of Vitamin D (Calciferol). Chem Rev. 1995;95(6):1877-1952.

* cited by examiner

*Primary Examiner* — Paul A Zucker
(74) *Attorney, Agent, or Firm* — Acuity Law Group, PC; Michael A. Whittaker

(57) ABSTRACT

It is an object of the present invention to provide methods for producing vitamin D that gives improved yields and reduced side product contamination. In various aspects, these methods provide for production of vitamin-$D_2$ using ergosterol as provitamin $D_2$ or a dihydroxy derivative thereof as a starting material, or production of vitamin-$D_3$ using 7-dehydrocholesterol as provitamin $D_3$ or a dihydroxy derivative thereof as the starting material. The methods described herein comprise irradiating the starting material in a solution including an organic or inorganic base with light in the wavelength range 245-360 nanometers (nm) to obtain a product containing pre-vitamin-$D_2$ or pre-vitamin-$D_3$, and heating the product to convert the resulting pre-vitamin-$D_2$ or pre-vitamin-$D_3$ to vitamin $D_2$ or vitamin $D_3$. In various embodiments, these methods further comprise recovering vitamin $D_2$ or vitamin $D_3$ from this reaction as a purified product.

7 Claims, 4 Drawing Sheets

METHODS FOR IMPROVED PRODUCTION OF VITAMINS $D_2$ AND $D_3$

CROSS-REFERENCE TO RELATED APPLICATIONS

This present invention is a continuation of U.S. patent application Ser. No. 15/537,391, filed 16 Jun. 2017, now U.S. Pat. No. 10,336,694, which is the U.S. national phase of International Patent Application No. PCT/US2015/066829, filed 18 Dec. 2015, which designated the United States and claims the benefit of United States Provisional Application No. 62/093,904 filed 18 Dec. 2014, each of which is hereby incorporated in its entirety including all tables, figures and claims.

BACKGROUND OF THE INVENTION

The following discussion of the background of the invention is merely provided to aid the reader in understanding the invention and is not admitted to describe or constitute prior art to the present invention.

Vitamin D refers to a group of fat-soluble secosteroids responsible for enhancing intestinal absorption of calcium, iron, magnesium, phosphate and zinc. In humans, the most important compounds in this group are vitamin $D_3$ (cholecalciferol) and vitamin $D_2$ (ergocalciferol). Vitamin D is naturally present in certain foods, added to others, and available as a dietary supplement.

SUMMARY OF THE INVENTION

It is an object of the present invention to provide methods for producing vitamin D that gives improved yields and reduced side product contamination. In various aspects, these methods provide for production of vitamin-$D_2$ using ergosterol as provitamin $D_2$ or a dihydroxy derivative thereof as a starting material, or production of vitamin-$D_3$ using 7-dehydrocholesterol as provitamin $D_3$ or a dihydroxy derivative thereof as the starting material. The methods described herein comprise irradiating the starting material in a solution including an organic or inorganic base with light in the wavelength range 245-360 nanometers (nm) to obtain a product containing pre-vitamin-$D_2$ or pre-vitamin-$D_3$, and heating the product to convert the resulting pre-vitamin-$D_2$ or pre-vitamin-$D_3$ to vitamin $D_2$ or vitamin $D_3$. In various embodiments, these methods further comprise recovering vitamin $D_2$ or vitamin $D_3$ from this reaction as a purified product.

Vitamin $D_3$ is the primary form of vitamin D in the human body produced through the action of ultraviolet irradiation (UV) on its provitamin 7-dehydrocholesterol. Human skin makes vitamin $D_3$ and supplies about 90% of vitamin D to humans. The transformation that converts 7-dehydrocholesterol to vitamin $D_3$ occurs in two steps. First, 7-dehydrocholesterol is photolyzed by ultraviolet light in a 6-electron conrotatory ring-opening electrocyclic reaction; the product is previtamin $D_3$. Second, previtamin $D_3$ spontaneously isomerizes to vitamin $D_3$ (cholecalciferol). At room temperature, the transformation of previtamin $D_3$ to vitamin $D_3$ in an organic solvent takes about 12 days to complete. The conversion of previtamin $D_3$ to vitamin $D_3$ in the skin is about 10 times faster than in an organic solvent. Vitamin $D_2$ is a derivative of ergosterol, a molecule which is not produced by humans. Thus, all Vitamin $D_2$ must be provided by diet. Vitamin $D_2$ is produced by some kinds of phytoplankton, invertebrates, yeasts, and fungi, and is produced by UV irradiation of its provitamin in a similar fashion to that of Vitamin $D_3$. The general scheme for conversion of Vitamins $D_2$ and $D_3$ is depicted in FIG. 4.

Conversion of ergosterol and 7-dehydrocholesterol to vitamin $D_2$ and $D_3$ involves ring opening of the B-ring of the sterol by ultraviolet (UV) activation of the conjugated diene. The absorbance of UV energy activates the molecule, and the $\pi \rightarrow \pi^*$ excitation (absorption, 250-310 nm; $\lambda max=291$ nm, $\varepsilon=12,000$) results in the opening of the 9,10 bond and the formation of the (Z)-hexadiene, previtamin $D_2$ or previtamin $D_3$. The UV irradiation of 7-dehydrocholesterol or ergosterol results in the steady diminution in concentration of the provitamin, initially giving rise to predominantly previtamin D. The previtamin levels reach a maximum as the provitamin level drops below ca 10%. The concentration of the previtamin then falls as it is converted to vitamin D, tachysterol and lumisterol, which increase in concentration with continued irradiation. Temperature, frequency of light, time of irradiation, and concentration of substrate all affect the ratio of products. The conversion of previtamin D at temperatures of ≤80° C. by thermal isomerization to give the cis vitamin (ergocalciferol) or cholecalciferol involves an equilibrium, as depicted in FIG. 3. Tian and Holick, J. Biol. Chem. 270: 8706-11, 1995; Hirsch, 2000, Vitamin D. in Kirk-Othmer Encyclopedia of Chemical Technology, DOI: 10.1002/0471238961.2209200108091819.a01

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

DETAILED DESCRIPTION OF THE INVENTION

Figure 1A:
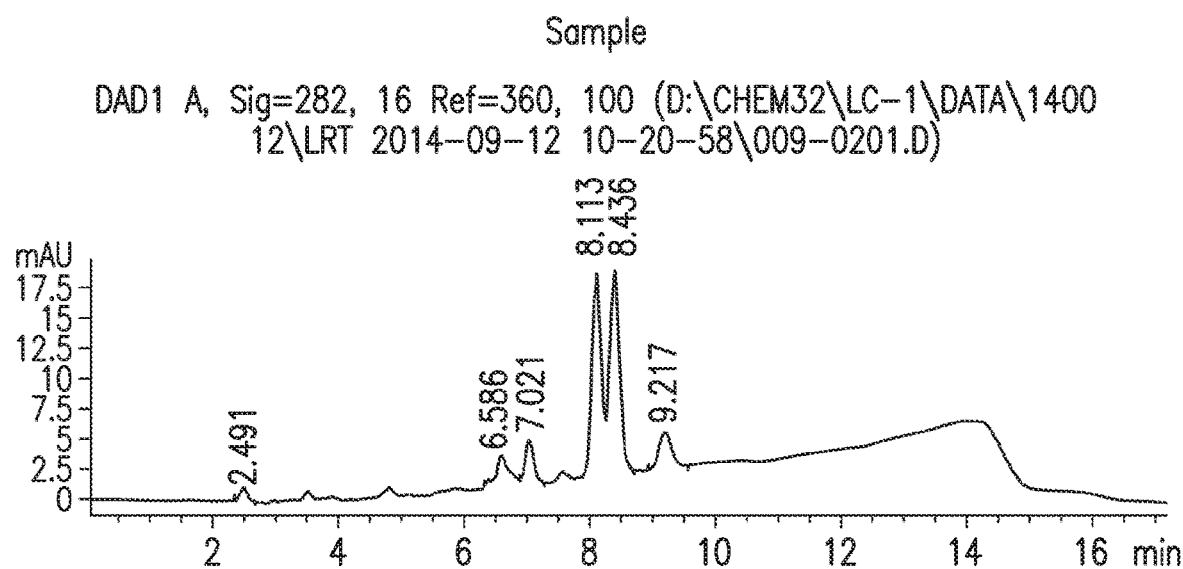
FIG. 1A depicts the HPLC recording at the wavelength of 282 nm for the detection and quantitation of 7-dehydrocholesterol (1), tachysterol (8) and lumisterol (7) and 1B depicts the HPLC recording at the wavelength of 265 nm for the detection and quantitation of Vitamin $D_3$ (4) and previtamin $D_3$ (6) in the experiment for the generation of Vitamin $D_3$ according to the methods of the present invention.
Figure 1B:
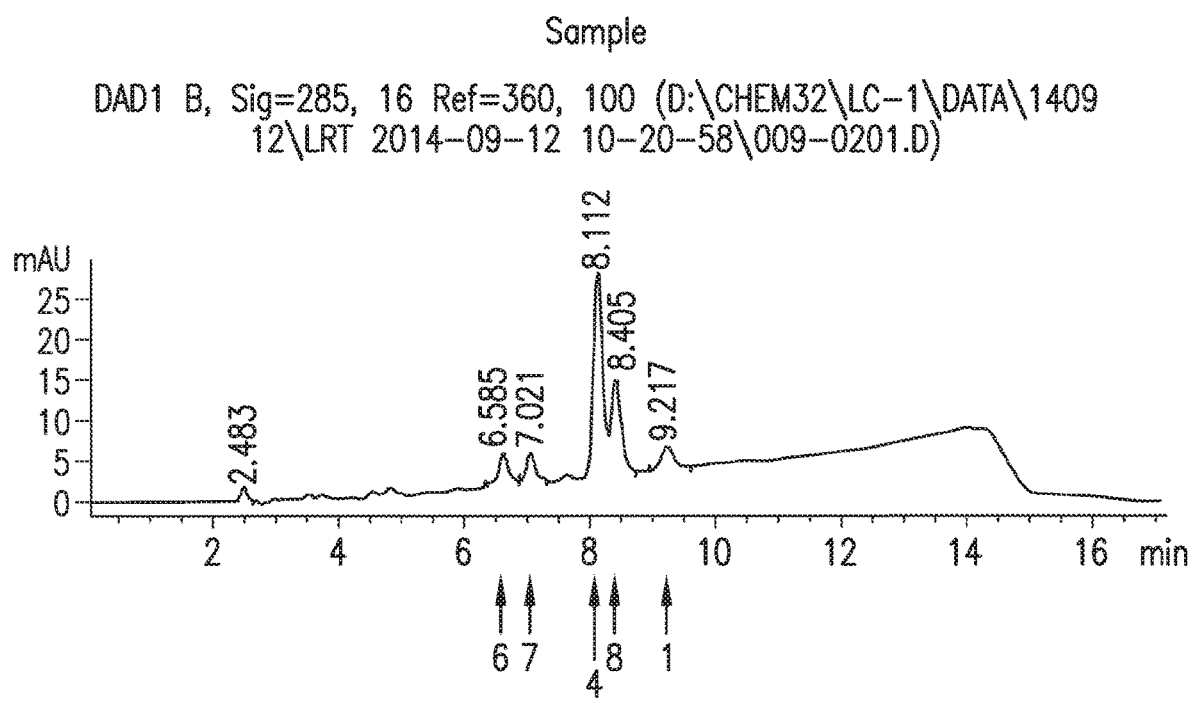
Figure 2A:
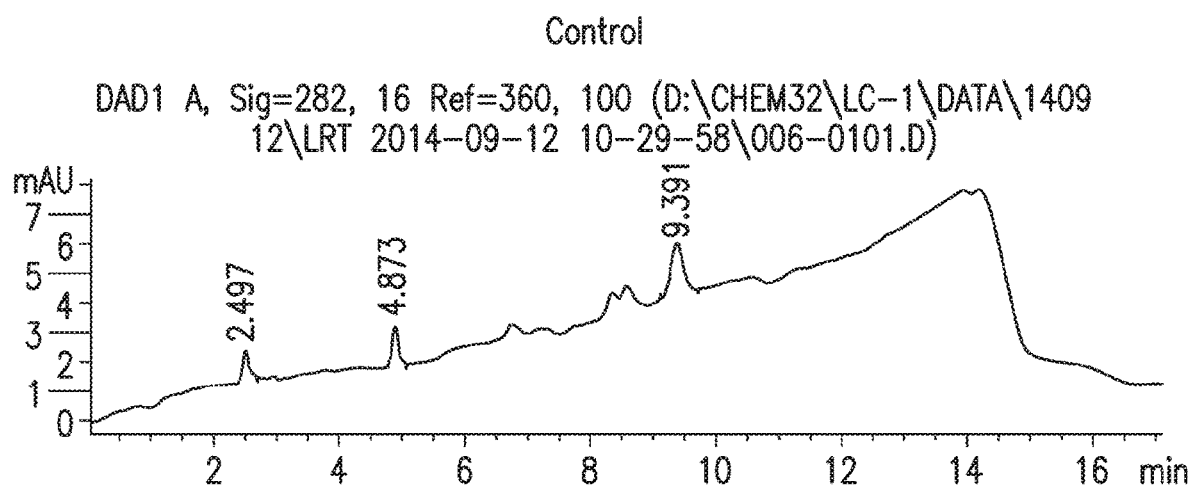
FIG. 2A depicts the HPLC recording at the wavelength of 282 nm for the detection and quantitation of 7-dehydrocholesterol, tachysterol and lumisterol and 2B depicts the HPLC recording at the wavelength of 265 nm for the detection and quantitation of Vitamin $D_3$ and previtamin $D_3$ in the control for the generation of Vitamin $D_3$ in the absence of base.
Figure 2B:
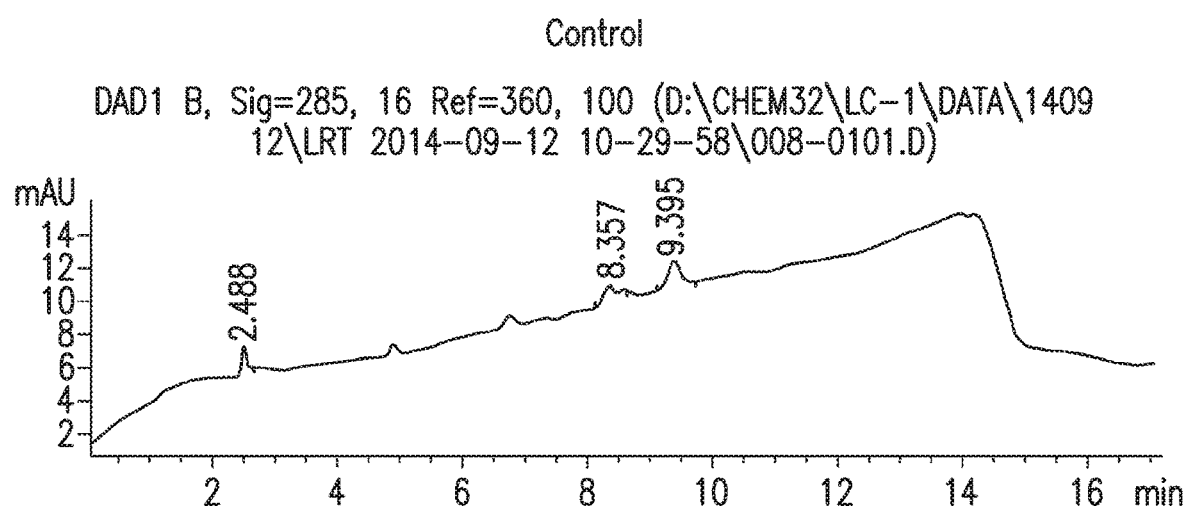
Figure 3:
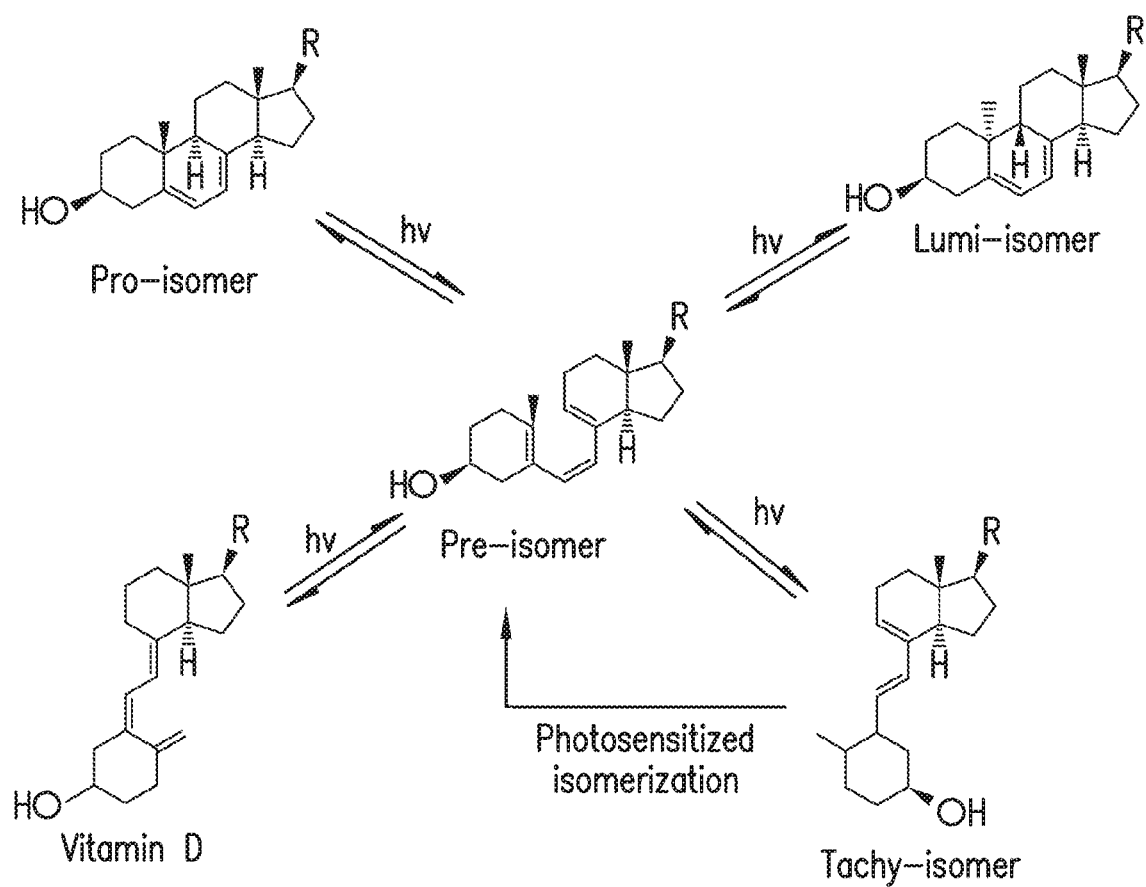
FIG. 3 depicts a general scheme for the photoconversion and thermoisomerization of Vitamin D from its precursor.
Figure 4:
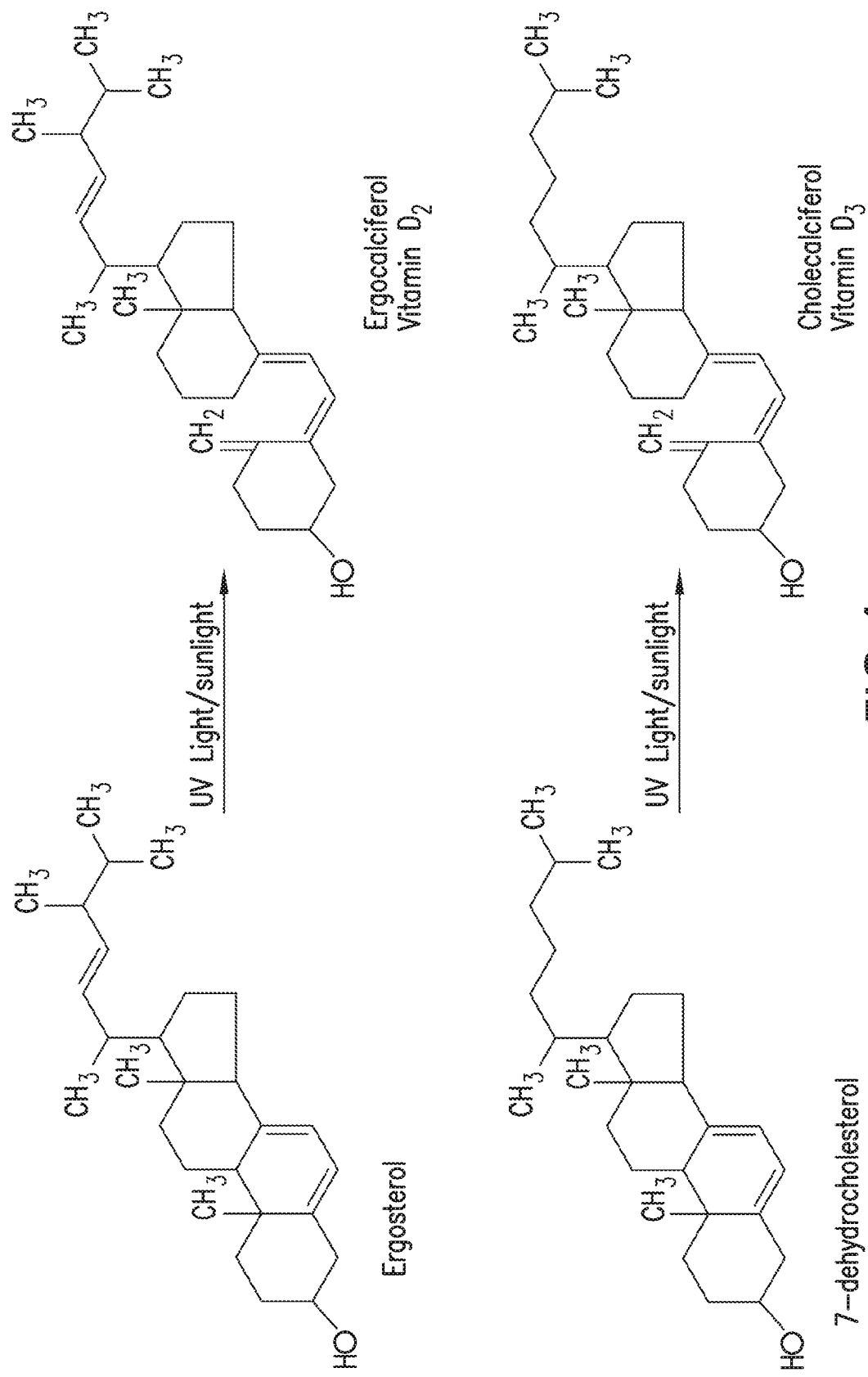
FIG. 4 depicts the structures of Vitamins $D_2$ and $D_3$ and their precursors.

As described herein, vitamin D may be prepared on a production scale by irradiating the provitamin 7-dehydrocholesterol or ergosterol in the presence of a base, and isomerizing the previtamin D formed in the irradiation. In the irradiation methods of the present invention, there are formed in addition to the previtamin other side products, especially lumisterol and tachysterol.

As noted above, the irradiation step occurs in the presence of an inorganic or organic base. In the case of an inorganic base, such a base can be selected from the group consisting of magnesium carbonate hydroxide, potassium hydrogen carbonate, sodium hydrogen carbonate, potassium carbonate, sodium carbonate, magnesium carbonate, calcium carbonate, barium carbonate, magnesium bicarbonate, ammonium hydroxide, lithium hydroxide, potassium hydroxide, sodium hydroxide, magnesium hydroxide, calcium hydroxide, magnesium-alumina hydroxide, magnesium oxide, calcium oxide, barium oxide, calcium silicate, magnesium silicate, magnesium aluminum silicate, magnesium aluminate, magnesium metasilicate-aluminate, sodium hydrogen phosphate, sodium dihydrogen phosphate, and synthetic hydrotalcite, or combinations thereof. This list is not meant to be limiting.

In the case of an organic base, such a base can be selected from the group consisting of an aliphatic amine or an aromatic amine; and in certain embodiments may be selected from the group consisting of methylamine, ethylamine, and isopropylamine, phenylamine (a.k.a. aniline), imidazole, benzimidazole, histidine, monoethanolamine, diethanolamine, triethanolamine, triethylamine, tripropylamine, tributylamine, dicyclohexylmethylamine, dicyclohexylamine, N,N'-dibenzylethylenediamine, and N-methylpyrrolidine or combinations thereof. This list is not meant to be limiting.

In order to effectively irradiate the starting material in a solution comprising an organic or inorganic base with light in the desired wavelength range as described herein\, the solution preferably comprises a solvent that is substantially transparent to light in the desired wavelength range. The term "substantially transparent" refers to a solvent which permits sufficient light to reach the starting material in order to convert at least 10% of the starting material, more preferably at least 25%, still more preferably at least 35%, and most preferably 45% to the desired product within 120 minutes. Conversion may be monitored using standard analytical methods such as HPLC on a reverse phase C18 column and UV absorbance detection. See, e.g., Kaushik et al., Food Chemistry 151: 225-30, 2014.

In certain embodiments, the solution comprises a solvent selected from the group consisting of an alcohol, an alkene, a polar solvent, a cycloalkane, an ether, a carboylic acid ester, and an aromatic solvent, or mixtures thereof. In preferred embodiments, the solution comprises a solvent selected from the group consisting of acetonitrile, toluene, pyridine, trichloroethylene, acetone, 1,2-ethanediol, ethanol, methanol, isopropanol, diethyl ether, methyl tert-butyl ether, ethyl acetate, dimethylsulfoxide, dimethylformamide, diethylamine, chloroform, anisole, benzene, 1-butanol, chloroform, cyclohexane, acetic acid butyl ester, hexane, 2-propanol, 1-hexene, naphthalene, tetrahydrofuran, m-xylene, p-xylene, o-xylene, n-methyl-2-pyrrolidone, 1,3-butadiene, and hexadecane, or mixtures thereof. This list is not meant to be limiting. The selection of base may be made on the basis of miscibility in the desired solvent.

The relative proportion of base:solvent can range from 1:99 to 100:0. In preferred embodiments, the relative proportion is from 5:95 to 100:0, and more preferably from 10:90 to 100:0 on a v:v basis of saturated or neat solutions of the base and solvent. By way of example, triethylamine is available as a >99% neat solution; dibenzylethylenediamine as a 97% solution; ammonium hydroxide as a 30% solution.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic and/or linear or branched unless otherwise specified. Primary, secondary, and tertiary alkyl groups are derived by removal of a hydrogen atom from a primary, secondary, and tertiary carbon atom, respectively, of an alkane. The n-alkyl group can be derived by removal of a hydrogen atom from a terminal carbon atom of a linear alkane. The groups RCH¾ (R≠H), $R_2CH(R\ne H)$, and R3C(R≠H) are primary, secondary, and tertiary alkyl groups, respectively.

A cycloalkane is a saturated cyclic hydrocarbon, with or without side chains, for example, cyclobutane. Other identifiers can be utilized to indicate the presence of particular groups in the cycloalkane (e.g., halogenated cycloalkane indicates that the presence of one or more halogen atoms replacing an equivalent number of hydrogen atoms in the cycloalkane). Unsaturated cyclic hydrocarbons having one endocyclic double or one triple bond are called cycloalkenes and cycloalkynes, respectively. Those having more than one such multiple bond are cycloalkadienes, cycloalkatrienes, and so forth. Other identifiers can be utilized to indicate the presence of particular groups in the cycloalkenes, cycloalkadienes, cycloalkatrienes, and so forth.

A "cycloalkyl group" is a univalent group derived by removing a hydrogen atom from a ring carbon atom of a cycloalkane.

Similarly, a "cycloalkylene group" refers to a group derived by removing two hydrogen atoms from a cycloalkane, at least one of which is a ring carbon. Thus, a "cycloalkylene group" includes a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane.

The term "alkene" whenever used in this specification and claims refers a linear or branched hydrocarbon olefin that has one carbon-carbon double bond and the general formula $C_nH_{2n}$. Alkadienes refer to a linear or branched hydrocarbon olefin having two carbon-carbon double bonds and the general formula $C_nH_{2n-2}$, and alkatrienes refer to linear or branched hydrocarbon olefins having three carbon-carbon and the general formula $C_nH_{2n-4}$. Alkenes, alkadienes, and alkatrienes can be further identified by the position of the carbon-carbon double bond(s). Other identifiers can be utilized to indicate the presence or absence of particular groups within an alkene, alkadiene, or alkatriene. For example, a haloalkene refers to an alkene having one or more hydrogen atoms replace with a halogen atom.

An "alkenyl group" is a univalent group derived from an alkene by removal of a hydrogen atom from any carbon atom of the alkene. Thus, "alkenyl group" includes groups in which the hydrogen atom is formally removed from an sp$^2$ hybridized (olefinic) carbon atom and groups in which the hydrogen atom is formally removed from any other carbon atom. For example and unless otherwise specified, 1-propenyl (—CH═CHCH$_3$), 2-propenyl (—CH$_2$CH═CH$_2$), and 3-butenyl (—CH$_2$CH$_2$CH═CH$_2$) groups are encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as necessary for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond can both be specified. Other identifiers can be utilized to indicate the presence or absence of particular groups within an alkene group. Alkene groups can also be further identified by the position of the carbon-carbon double bond.

An arene is an aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), of which is shown here.

An "ether" is any of a class of organic compounds in which two hydrocarbon groups are linked by an oxygen atom.

As used herein, the term "polar solvent" means those solvents that have a hydrogen bonding solubility parameter greater than 9. See "Hansen Solubility Parameters", Charles M. Hansen, ISBN0-8493-7248-8 for definition of Hydrogen Bonding Solubility Parameter.

As used herein, the term "non-polar solvent" refers to a compound which is immiscible with an ionic liquid. In one embodiment, the term "non-polar solvent" refers to a solvent which has a dielectric constant of no more than 5, preferably no more than 3.0, more preferably no more than 2.5, measured at 20° C. and atmospheric pressure according to ASTM D924-92. In a preferred embodiment, the term "non-polar solvent" refers to cyclic and acyclic aliphatic hydrocarbons, and particularly cyclic and acyclic saturated aliphatic hydrocarbons, i.e. alkanes and cycloalkanes, such as pentanes, hexanes, heptanes, octanes and cyclohexane etc. Said non-polar aliphatic hydrocarbons may be substituted by one or more halogen atoms, the same or different, but are preferably unsubstituted.

As used herein, the term "carboxylic acid ester" refers to the mono- or diesters of carboxylic acids, respectively, having the following formula:

wherein R$_1$ is a C1 to C6 hydrocarbyl group independently selected from the group consisting of alkyl, cycloalkyl, and aryl; said hydrocarbyl group optionally substituted with at least one hydroxyl group and R$_2$ is a C1 to C4 (1 to 4 carbon atoms) straight chain or branched chain alkyl groups. In a preferred embodiment, R$_2$ is an ethanol or methanol. As used herein, the term "carboxylic acid" will be used to refer carboxylic acids having the following formula:

wherein R$_1$ is a C1 to C6 hydrocarbyl group independently selected from the group consisting of alkyl, cycloalkyl, and aryl; said hydrocarbyl group optionally substituted with at least one hydroxyl group.

In preferred embodiments, the solvent selected also serves as the base for the reaction. By way of example, triethylamine serving as both solvent and base that also offers the additional advantage of being easily removed by distillation and by azeotropic distillation.

Suitable irradiation conditions comprise placing the solution having a concentration of between about 0.5 and 10 g/L of the 7-dehydrocholesterol or ergosterol into a UV-transparent reactor such as one made of quartz, polyethylene, polypropylene, etc. and exposing the solution to UV light. Alternatively, a reactor equipped with submersible quartz well, holding the UV lamp, can be used. The UV exposure time is optimized for every device configuration used. In the present methods, the loss of any of the isomers is inhibited and the reaction can achieve an equilibrium that is insensitive to irradiation time. By continuously adding the 7-dehydrocholesterol or ergosterol starting material to the reaction to replenish it at the rate of its conversion in the photochemical reaction, a concentration of between about 10 g/L to about 80 g/L or more of the reaction products may be achieved. Preferably, a reaction product of from 20 g/L to 40 g/L or more is obtained for use in the thermoisomerization step which may follow. The thermoisomerization step can be carried out in the same solution as the irradiation step, or in a different solution. Most preferably the thermoisomerization step is carried out in the same solution as the irradiation step.

Typical light sources comprise low pressure mercury lamps, medium pressure mercury lamps, light-emitting diodes (LEDs), nitrogen lasers which function at 337 nm, or a YAG lasers which function at 353 nm, XeF lasers which function at 350 nm, Raman shifted XeCl lasers, and broadband dye lasers pumped by XeCl or KrF excimer lasers, the last two being tunable to operate as required in the 330-360 nm range. The temperature of the solution during irradiation may be held in the range 0°-10° C., or in a range as desired;

The peak wavelength value for UV conversion of vitamin D occurs at about 295 nm, with a broad action spectrum providing useful light from about 245-360 nm. Preferred wavelengths are between about 250 nm and about 320 nm, and more preferably between about 270 nm and about 300 nm. See, e.g., Olds et al., NIWA UV Workshop, Poster 53, Queenstown Apr. 7-9, 2010. If desired, the irradiation may be performed in steps, e.g., a first irradiation in the wavelength range 245-260 nm, followed by a second irradiation in the wavelength range 300-350 nm.

While heating is not absolutely required, the rate of conversion of precursor which converts to vitamin D increases with temperature. Yates et al., in Vitamin D: Molecular, Cellular and Clinical Endocrinology. Proceedings of the Seventh Workshop on Vitamin D, Rancho Mirage, Calif., USA, April 1988, pp. 83-92. Thus, it is preferred that following the irradiation step, the product is heated to between about 50° C. and about 150° C. for at least 2 hours (hrs), leading to a process called "thermoisomerization" to effect conversion from pre-vitamin-D$_2$ or pre-vitamin-D₃ to vitamin D₂ or vitamin D₃. In certain embodiments, the product is heated to between about 40° C. and about 120° C., and still more preferably to between about 75° C. and about 90° C. for between 3 hours and 16 hours.

Typically, a yield of at least 10%, more preferably at least 25%, still more preferably at least 35%, and most preferably 45% or more of vitamin $D_2$ or vitamin $D_3$ is produced from the starting material. In certain embodiments, a significant concentration of lumisterol and tachysterol is produced. By "significant concentration" is meant at least 10% of the product yielded from the method comprises one or both of lumisterol and tachysterol, provided that the total yield of lumisterol and tachysterol is less than the yield of vitamin $D_2$ or vitamin $D_3$.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

A solution of 7-dehydrocholesterol (4.86 mg/mL) was prepared in ethanol. One milliliter of the 7-dehydrocholesterol solution was transferred to a quartz test tube. An organic base (triethylamine, 0.2 mL) was added. The test tube was sealed.

As a control, one milliliter of the 7-dehydrocholesterol solution was transferred to a quartz test tube. Ethanol (0.2 mL) was added in place of the organic base. The test tube was sealed.

Both test tubes were affixed side-by-side to a quartz immersion well and lowered into a water bath, the temperature of which was kept at 5-10° C. A Hanovia UV lamp model No. 608A036 was placed in the well 15 min. after it has been turned on. Both solutions were illuminated for 3 hrs.

Both the triethylamine-containing solution, as well as the control, were subsequently heated to 85° C. for 2.5 hrs. Both solutions were analyzed by HPLC as depicted in FIGS. 1A and B (base) and 2A and B (control). Legend to FIGS. 1A and B: 7-dehydrocholesterol (1), pre-vitamin D₃ (6), lumisterol (7), vitamin D₃ (4) and tachysterol (8). The yields obtained were as follows:

| Sample ID | Vitamin D₃ (mg/mL) | 7-dehydrocholesterol (mg/mL) |
|---|---|---|
| Ethanol/triethylamine | 1.08 | 0.305 |
| Control | 0.178 | <0.06 |

In addition to much higher vitamin D₃ yield and higher recovery of residual 7-dehydrocholesterol when the procedure was carried out in the presence of base, significant concentration of the three major isomers—pre-vitamin D, lumisterol and tachysterol—were present in the Sample, while none of them was detected in the control. The low concentration of vitamin D₃ as well as only traces of pro-vitamin D₃ (7-dehydrocholesterol) remaining in the Control as opposed to the high concentrations of the corresponding fractions in the Sample are evidence of significant photochemical degradation in absence, and significant improvement in the presence, of triethylamine.

Example 2

A solution of pro-vitamin D₃ (7-dehydrocholesterol) was prepared in methyl-tert-butyl ether at a concentration of 29.05 g/L. The solution was divided into two equal volumes. 0.1 vol. of base (DIBED=dibenzylethylenediamine) is added to one portion, and to equalize the volumes, 0.1 vol. of MTBE is added to the control.

One milliliter of each solution was transferred to a quartz test tube. The test tube was sealed. Both test tubes were affixed side-by-side to a quartz immersion well and lowered into a water bath, the temperature of which was kept at 5-10° C. A Hanovia UV lamp model No. 608A036 was placed in the well 15 min. after it has been turned on. Both solutions were illuminated for 3 hrs.

Both the dibenzylethylenediamine-containing solution, as well as the control, were subsequently heated to 85° C. for 2.5 hrs. Both solutions were analyzed by HPLC.

Conversion results from this experiment are presented in the following table:

| | 7-Dehydrocholesterol | | Vitamin D3 | |
|---|---|---|---|---|
| UV Exposure (Min.) | DIBED (mg/mL) | Control (mg/mL) | DIBED (mg/mL) | Control (mg/mL) |
| 0 | 29.05 | 29.05 | 0 | 0 |
| 10 | 25.53 | 18.76 | 2.07 | 2.12 |
| 20 | 23.29 | 13.29 | 3.38 | 3.4 |
| 30 | 20.29 | 9.67 | 4.62 | 4.16 |
| 50 | 16.05 | 7.35 | 6.84 | 4.87 |
| 90 | 9.89 | 1.78 | 8.77 | 5.04 |
| 120 | 7.45 | 1.42 | 9.74 | 5.36 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

I claim:

1. A method of production of vitamin-$D_2$ using ergosterol or a dihydroxy derivative thereof as a starting material, or production of vitamin-$D_3$ using 7-dehydrocholesterol or a dihydroxy derivative thereof as the starting material, comprising:
   (a) irradiating the starting material with ultraviolet light in a solution comprising a base selected from the group consisting of triethylamine, dibenzyl ethylenediamine, and an organic solvent having a dielectric constant greater than 5, to obtain a product containing pre-vitamin-$D_2$ or pre-vitamin-$D_3$; and
   (b) heating the product to convert the pre-vitamin-$D_2$ or pre-vitamin-$D_3$ to vitamin $D_2$ or vitamin $D_3$.

2. A method according to claim 1, wherein the basic solvent having a dielectric constant greater than 5 is tertrahydrofuran.

3. A method according to claim 1, wherein the product is heated to between 50° C. and 100° C. for at least 2 hours.

4. A method according to claim 3, wherein the product is heated to between 75° C. and 90° C. for between 3 hours and 16 hours.

5. A method according to claim 1, wherein a yield of at least 25% of vitamin $D_2$ or vitamin $D_3$ is produced.

6. A method according to claim 1, wherein following the heating step, one or both of lumisterol and tachysterol comprise at least 10% of the products produced from the starting material, provided that the total yield of lumisterol and tachysterol is less than the yield of vitamin $D_2$ or vitamin $D_3$.

7. A method according to claim 6, wherein the solution comprises no solvent other than the base.

* * * * *